US011395865B2

(12) United States Patent
Kladakis et al.

(10) Patent No.: US 11,395,865 B2
(45) Date of Patent: Jul. 26, 2022

(54) SCAFFOLDS WITH VIABLE TISSUE

(75) Inventors: Stephanie M. Kladakis, Watertown, MA (US); Sridevi Dhanaraj, Raritan, NJ (US); Robert Boock, Braintree, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1497 days.

(21) Appl. No.: 10/775,034

(22) Filed: Feb. 9, 2004

(65) Prior Publication Data

US 2005/0177249 A1    Aug. 11, 2005

(51) Int. Cl.
| | |
|---|---|
| *A61F 2/30* | (2006.01) |
| *A61L 27/56* | (2006.01) |
| *A61L 27/58* | (2006.01) |
| *A61L 27/48* | (2006.01) |

(52) U.S. Cl.
CPC ............. *A61L 27/48* (2013.01); *A61L 27/56* (2013.01); *A61L 27/58* (2013.01)

(58) Field of Classification Search
CPC ...... A61L 27/48; A61L 27/56; A61L 27/3817; A61L 27/3654; A61L 2430/06; A61F 2002/4648; A61F 2230/0086; A61F 2/2846; A61F 2/28; A61F 2002/3023; A61F 2002/30766; A61B 17/8095; A61B 17/864
USPC .... 623/8, 23.64, 23.75, 23.76, 14.12, 21.15; 424/422–426, 572
See application file for complete search history.

(56) References Cited

U.S. PATENT DOCUMENTS

| | | | |
|---|---|---|---|
| 3,272,204 | A | 9/1966 | Artandi |
| 3,562,820 | A | 2/1971 | Braun |
| 3,739,402 | A | 6/1973 | Cooley et al. |
| 3,812,017 | A | 5/1974 | Santangelo et al. |
| 3,857,932 | A | 12/1974 | Shepard et al. |
| 4,045,418 | A | 8/1977 | Sinclair |

(Continued)

FOREIGN PATENT DOCUMENTS

| | | |
|---|---|---|
| AU | 717552 | 3/1998 |
| CA | 2247158 | 8/1997 |

(Continued)

OTHER PUBLICATIONS

Bonisch, M., et al. "Septumredonstrucktion mit PDS-Folie" HNO 47: 1999 pp. 546-550.

(Continued)

*Primary Examiner* — Brian E Pellegrino

(57) ABSTRACT

A composite implant is provided for repairing a tissue defect in a patient. In one embodiment, the implant is a porous tissue scaffold having at least one pocket formed therein and adapted to contain a viable tissue. The tissue scaffold can have a variety of configurations, and in one embodiment it includes top and bottom portions that can be at least partially mated to one another, and in an exemplary embodiment that are heated sealed to one another around a perimeter thereof to form an enclosed pocket therebetween. The pocket is preferably sealed with a viable tissue disposed therein. In another embodiment, the tissue scaffold is substantially wedge-shaped and the pocket comprises a hollow interior formed in the tissue scaffold, and/or at least one lumen extending into the tissue scaffold. The tissue scaffold can also optionally include at least one surface feature formed thereof to promote blood vessel formation.

29 Claims, 7 Drawing Sheets

(56) References Cited

U.S. PATENT DOCUMENTS

| | | |
|---|---|---|
| 4,057,537 A | 11/1977 | Sinclair |
| 4,105,034 A | 8/1978 | Shalaby et al. |
| 4,130,639 A | 12/1978 | Shalaby et al. |
| 4,130,689 A | 12/1978 | Costa, Jr. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,344,193 A | 8/1982 | Kenny |
| 4,520,821 A | 6/1985 | Schmidt et al. |
| 4,553,272 A | 11/1985 | Mears |
| 4,585,458 A | 4/1986 | Kurland |
| 4,597,766 A | 7/1986 | Hilal et al. |
| 4,609,551 A | 9/1986 | Caplan et al. |
| 4,728,329 A | 3/1988 | Mansat et al. |
| 4,801,299 A | 1/1989 | Brendel et al. |
| 4,837,285 A | 6/1989 | Berg et al. |
| 4,902,508 A | 2/1990 | Badylak et al. |
| 4,917,700 A | 4/1990 | Kins |
| 4,946,377 A | 8/1990 | Kovach |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,078,744 A | 1/1992 | Chvapil |
| 5,108,807 A | 4/1992 | Tucker |
| 5,108,989 A | 4/1992 | Amento et al. |
| 5,147,400 A | 9/1992 | Kaplan et al. |
| 5,176,708 A | 1/1993 | Frey et al. |
| 5,206,023 A | 4/1993 | Hunziker |
| 5,258,028 A | 11/1993 | Ersek et al. |
| 5,263,984 A | 11/1993 | Li et al. |
| 5,290,494 A | 3/1994 | Coombes et al. |
| 5,306,311 A | 4/1994 | Stone |
| 5,320,624 A | 6/1994 | Kaplan et al. |
| 5,320,646 A | 6/1994 | Patton et al. |
| 5,326,357 A | 7/1994 | Kandel |
| 5,366,756 A | 11/1994 | Chesterfield et al. |
| 5,393,594 A | 2/1995 | Koyfman et al. |
| 5,425,766 A | 6/1995 | Bowaid |
| 5,443,950 A | 8/1995 | Naughton et al. |
| 5,445,833 A | 8/1995 | Badylak et al. |
| 5,455,041 A | 10/1995 | Genco et al. |
| 5,464,929 A | 11/1995 | Bezwada et al. |
| 5,468,253 A | 11/1995 | Bezwada et al. |
| 5,480,827 A | 1/1996 | Guillemin et al. |
| 5,487,897 A | 1/1996 | Polson et al. |
| 5,514,181 A | 5/1996 | Light et al. |
| 5,514,378 A | 5/1996 | Mikos et al. |
| 5,571,189 A * | 11/1996 | Kuslich ............... 623/17.12 |
| 5,577,517 A | 11/1996 | Bonutti |
| 5,589,176 A | 12/1996 | Seare, Jr. |
| 5,595,751 A | 1/1997 | Bezwada et al. |
| 5,597,579 A | 1/1997 | Bezwada et al. |
| 5,607,687 A | 3/1997 | Bezwada et al. |
| 5,612,028 A | 3/1997 | Sackier et al. |
| 5,618,552 A | 4/1997 | Bezwada et al. |
| 5,620,698 A | 4/1997 | Bezwada et al. |
| 5,624,463 A | 4/1997 | Stone et al. |
| 5,626,611 A | 5/1997 | Liu et al. |
| 5,632,745 A | 5/1997 | Schwartz |
| 5,634,879 A | 6/1997 | Mueller-Glauser et al. |
| 5,645,850 A | 7/1997 | Bezwada et al. |
| 5,648,088 A | 7/1997 | Bezwada et al. |
| 5,654,135 A | 8/1997 | Tinois et al. |
| 5,656,492 A | 8/1997 | Giowacke et al. |
| 5,677,355 A | 10/1997 | Shalaby et al. |
| 5,681,353 A | 10/1997 | Li et al. |
| 5,697,976 A | 12/1997 | Chesterfield et al. |
| 5,698,213 A | 12/1997 | Jamiolkowski et al. |
| 5,700,583 A | 12/1997 | Jamiolkowski et al. |
| 5,705,181 A | 1/1998 | Cooper et al. |
| 5,709,854 A | 1/1998 | Griffith-Cima et al. |
| 5,711,960 A | 1/1998 | Shikinami |
| 5,713,920 A | 2/1998 | Bezwada et al. |
| 5,720,969 A | 2/1998 | Gentile et al. |
| 5,723,331 A | 3/1998 | Tubo et al. |
| 5,735,903 A | 4/1998 | Li et al. |
| 5,736,372 A | 4/1998 | Vacanti et al. |
| 5,755,791 A | 5/1998 | Whitson et al. |
| 5,759,190 A | 6/1998 | Vibe-Hansen et al. |
| 5,766,631 A | 6/1998 | Arnold |
| 5,769,897 A * | 6/1998 | Harle ..................... A61L 27/48<br>623/23.61 |
| 5,769,899 A | 6/1998 | Schwartz et al. |
| 5,782,914 A | 7/1998 | Schankereli |
| 5,786,217 A | 7/1998 | Tubo et al. |
| 5,800,537 A | 9/1998 | Bell |
| 5,800,543 A | 9/1998 | McLeod et al. |
| 5,830,493 A | 11/1998 | Yokota et al. |
| 5,837,235 A | 11/1998 | Mueller et al. |
| 5,837,278 A | 11/1998 | Geistlich et al. |
| 5,842,477 A | 12/1998 | Naughton et al. |
| 5,855,608 A | 1/1999 | Brekke et al. |
| 5,859,150 A | 1/1999 | Jamiolkowski et al. |
| 5,865,849 A * | 2/1999 | Stone .................. A61L 27/3654<br>128/898 |
| 5,891,558 A | 4/1999 | Bell et al. |
| 5,902,741 A | 5/1999 | Purchio et al. |
| 5,904,716 A | 5/1999 | Gendler |
| 5,904,717 A | 5/1999 | Brekke et al. |
| 5,914,121 A | 6/1999 | Robey et al. |
| 5,922,025 A | 7/1999 | Hubbard |
| 5,964,805 A | 10/1999 | Stone |
| 5,968,096 A | 10/1999 | Whitson et al. |
| 5,980,889 A | 11/1999 | Butler et al. |
| 5,989,269 A | 11/1999 | Vibe-Hanen et al. |
| 5,990,194 A | 11/1999 | Dunn et al. |
| 5,990,378 A | 11/1999 | Ellis |
| 6,001,352 A | 12/1999 | Boyan et al. |
| 6,001,394 A | 12/1999 | Daculsi et al. |
| 6,005,161 A | 12/1999 | Brekke et al. |
| 6,008,433 A * | 12/1999 | Stone .................. A61B 17/8095<br>623/23.47 |
| 6,027,742 A | 2/2000 | Lee et al. |
| 6,042,534 A | 3/2000 | Gellman et al. |
| 6,042,610 A | 3/2000 | Li et al. |
| 6,054,122 A | 4/2000 | MacPhee et al. |
| 6,077,989 A | 6/2000 | Kandel et al. |
| 6,080,579 A | 6/2000 | Hanley, Jr. et al. |
| 6,096,532 A | 8/2000 | Armstrong et al. |
| 6,103,255 A | 8/2000 | Levene et al. |
| 6,110,209 A | 8/2000 | Stone |
| 6,110,212 A | 8/2000 | Gregory |
| 6,113,640 A | 9/2000 | Tormala et al. |
| 6,117,166 A | 9/2000 | Winston et al. |
| 6,120,514 A | 9/2000 | Vibe-Hansen et al. |
| 6,121,042 A | 9/2000 | Peterson et al. |
| 6,123,727 A | 9/2000 | Vacanti et al. |
| 6,132,463 A | 10/2000 | Lee et al. |
| 6,132,468 A | 10/2000 | Mansmann |
| 6,139,578 A | 10/2000 | Lee et al. |
| 6,140,039 A | 10/2000 | Naughton et al. |
| 6,143,293 A | 11/2000 | Weiss et al. |
| 6,147,135 A | 11/2000 | Yuan et al. |
| 6,153,292 A | 11/2000 | Bell et al. |
| 6,156,068 A | 12/2000 | Walter et al. |
| 6,165,217 A | 12/2000 | Hayes |
| 6,171,338 B1 | 1/2001 | Talja et al. |
| 6,176,880 B1 | 1/2001 | Plouhar et al. |
| 6,179,840 B1 | 1/2001 | Bowman |
| 6,179,872 B1 | 1/2001 | Bell et al. |
| 6,180,007 B1 | 1/2001 | Gentile et al. |
| 6,183,737 B1 | 2/2001 | Zaleske et al. |
| 6,187,053 B1 | 2/2001 | Minuth |
| 6,187,329 B1 | 2/2001 | Agrawal et al. |
| 6,197,061 B1 | 3/2001 | Masuda et al. |
| 6,197,325 B1 | 3/2001 | MacPhee et al. |
| 6,200,606 B1 * | 3/2001 | Peterson ............. A61L 27/3817<br>424/93.7 |
| 6,214,045 B1 | 4/2001 | Corbitt, Jr. et al. |
| 6,214,055 B1 | 4/2001 | Simionescu et al. |
| 6,242,247 B1 | 6/2001 | Rieser et al. |
| 6,251,673 B1 | 6/2001 | Winkler |

(56) References Cited

U.S. PATENT DOCUMENTS

| | | |
|---|---|---|
| 6,277,151 B1 | 8/2001 | Lee et al. |
| 6,283,980 B1 | 9/2001 | Vibe-Hansen et al. |
| 6,287,316 B1 | 9/2001 | Agarwal et al. |
| 6,287,340 B1 | 9/2001 | Altman et al. |
| 6,291,240 B1 | 9/2001 | Mansbridge et al. |
| 6,306,177 B1 | 10/2001 | Felt et al. |
| 6,306,424 B1 | 10/2001 | Vyakarnam et al. |
| 6,316,692 B1 | 11/2001 | Readhead et al. |
| 6,319,712 B1 | 11/2001 | Meenen et al. |
| 6,328,765 B1 | 12/2001 | Hardwick et al. |
| 6,331,312 B1 | 12/2001 | Lee et al. |
| 6,333,029 B1 | 12/2001 | Vyakarnam et al. |
| 6,365,149 B2 | 4/2002 | Vyakarnam et al. |
| 6,378,527 B1 | 4/2002 | Hungerford et al. |
| 6,378,572 B1 | 4/2002 | Neubauer et al. |
| 6,379,367 B1 | 4/2002 | Vibe-Hansen et al. |
| 6,464,729 B1 | 10/2002 | Kandel |
| 6,485,723 B1 | 11/2002 | Badylak et al. |
| 6,489,165 B2 | 12/2002 | Bhatnagar et al. |
| 6,503,278 B1 | 1/2003 | Pohjonen et al. |
| 6,511,511 B1 | 1/2003 | Slivka et al. |
| 6,511,958 B1 | 1/2003 | Atkinson et al. |
| 6,521,430 B1 | 2/2003 | Orwar et al. |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,551,355 B1 | 4/2003 | Lewandrowski et al. |
| 6,569,172 B2 | 5/2003 | Asculai et al. |
| 6,592,588 B1 | 7/2003 | Bobic et al. |
| 6,599,323 B2 | 7/2003 | Melican et al. |
| 6,605,294 B2 | 8/2003 | Sawhney |
| 6,626,950 B2 | 9/2003 | Brown et al. |
| 6,652,450 B2 | 11/2003 | Neisz et al. |
| 6,652,585 B2 | 11/2003 | Lange |
| 6,727,224 B1 | 4/2004 | Zhang et al. |
| 6,773,458 B1 | 8/2004 | Brauker et al. |
| 6,783,712 B2 | 8/2004 | Slivka et al. |
| 6,840,962 B1 | 1/2005 | Vacanti et al. |
| 6,852,330 B2 | 2/2005 | Bowman et al. |
| 6,866,681 B2 | 3/2005 | Laboureau et al. |
| 6,884,428 B2 | 4/2005 | Binette et al. |
| 6,886,568 B2 | 5/2005 | Frondoza et al. |
| 6,886,569 B2 | 5/2005 | Chervitz et al. |
| 6,902,932 B2 | 6/2005 | Altman et al. |
| 7,109,034 B2 | 9/2006 | Orwar et al. |
| 7,208,177 B2 | 4/2007 | Geistlich et al. |
| 7,262,020 B2 | 8/2007 | Hellerstein |
| 7,316,822 B2 | 1/2008 | Binette et al. |
| 7,368,124 B2 | 5/2008 | Chun et al. |
| 7,456,012 B2 | 11/2008 | Ryttsen et al. |
| 7,799,089 B2 | 9/2010 | Plouhar et al. |
| 7,824,701 B2 | 11/2010 | Binette et al. |
| 7,875,296 B2 | 1/2011 | Binette et al. |
| 7,901,461 B2 | 3/2011 | Harmon et al. |
| 8,137,686 B2 | 3/2012 | Kladakis et al. |
| 8,137,702 B2 | 3/2012 | Binette et al. |
| 8,197,837 B2 | 6/2012 | Jamiolkowski et al. |
| 8,221,780 B2 | 7/2012 | Dhanaraj et al. |
| 8,226,715 B2 | 7/2012 | Hwang et al. |
| 8,496,970 B2 | 7/2013 | Binette et al. |
| 8,637,066 B2 | 1/2014 | Binnette et al. |
| 8,641,775 B2 | 2/2014 | Harmon et al. |
| 8,691,259 B2 | 4/2014 | Bowman et al. |
| 8,895,045 B2 | 11/2014 | Jamiolkowski et al. |
| 9,211,362 B2 | 12/2015 | Hwang et al. |
| 9,511,171 B2 | 12/2016 | Binette et al. |
| 10,583,220 B2 | 3/2020 | Binette et al. |
| 10,603,408 B2 | 3/2020 | Binette et al. |
| 2001/0014475 A1 | 8/2001 | Frondoza et al. |
| 2001/0016353 A1 | 8/2001 | Janas et al. |
| 2001/0016772 A1 | 8/2001 | Lee et al. |
| 2001/0023373 A1 | 9/2001 | Plouhar et al. |
| 2001/0033857 A1 | 10/2001 | Vyakarnam et al. |
| 2001/0038848 A1 | 11/2001 | Donda et al. |
| 2001/0039453 A1 | 11/2001 | Gresser et al. |
| 2001/0051834 A1 | 12/2001 | Frondoza et al. |
| 2001/0053353 A1 | 12/2001 | Griffith et al. |
| 2001/0053839 A1 | 12/2001 | Noishiki et al. |
| 2002/0006428 A1 | 1/2002 | Mahmood et al. |
| 2002/0009477 A1 | 1/2002 | Mahmood et al. |
| 2002/0009805 A1 | 1/2002 | Nevo et al. |
| 2002/0009806 A1 | 1/2002 | Hicks, Jr. |
| 2002/0013627 A1 | 1/2002 | Geistlich et al. |
| 2002/0015719 A1 | 2/2002 | Kellner et al. |
| 2002/0022883 A1 | 2/2002 | Burg |
| 2002/0022884 A1 | 2/2002 | Mansmann |
| 2002/0028192 A1 | 3/2002 | Dimitrijevich et al. |
| 2002/0029055 A1 | 3/2002 | Bonutti |
| 2002/0062151 A1 | 5/2002 | Altman et al. |
| 2002/0082631 A1 | 6/2002 | Bonutti |
| 2002/0083479 A1 | 6/2002 | Winston et al. |
| 2002/0091403 A1 | 7/2002 | Bonutti |
| 2002/0091406 A1 | 7/2002 | Bonutti |
| 2002/0099401 A1 | 7/2002 | Bonutti |
| 2002/0099448 A1 | 7/2002 | Hiles et al. |
| 2002/0107570 A1 | 8/2002 | Sybert et al. |
| 2002/0119177 A1 | 8/2002 | Bowman et al. |
| 2002/0120348 A1 | 8/2002 | Melican et al. |
| 2002/0123750 A1 | 9/2002 | Eisermann et al. |
| 2002/0127265 A1 | 9/2002 | Bowman et al. |
| 2002/0133229 A1 | 9/2002 | Laurencin et al. |
| 2002/0133235 A1 | 9/2002 | Hungerford et al. |
| 2002/0150604 A1 | 10/2002 | Yi et al. |
| 2002/0151975 A1 | 10/2002 | Farr et al. |
| 2002/0173558 A1 | 11/2002 | Williams et al. |
| 2002/0176893 A1 | 11/2002 | Wironen et al. |
| 2002/0177224 A1 | 11/2002 | Madry et al. |
| 2003/0003153 A1 | 1/2003 | Asculai et al. |
| 2003/0004578 A1 | 1/2003 | Brown et al. |
| 2003/0012805 A1 | 1/2003 | Chen et al. |
| 2003/0023316 A1 | 1/2003 | Brown et al. |
| 2003/0026787 A1 | 2/2003 | Fearnot et al. |
| 2003/0027332 A1 | 2/2003 | Lafrance et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0045937 A1 | 3/2003 | Ginn |
| 2003/0050709 A1 | 3/2003 | Noth et al. |
| 2003/0064917 A1 | 4/2003 | Crawford et al. |
| 2003/0075822 A1 | 4/2003 | Slivka et al. |
| 2003/0077311 A1 | 4/2003 | Vyakarnam et al. |
| 2003/0078617 A1* | 4/2003 | Schwartz et al. ............ 606/230 |
| 2003/0147935 A1 | 8/2003 | Binette et al. |
| 2003/0193104 A1 | 10/2003 | Melican et al. |
| 2004/0024457 A1 | 2/2004 | Boyce et al. |
| 2004/0033212 A1* | 2/2004 | Thomson ............ A61L 27/3817 623/23.63 |
| 2004/0059416 A1 | 3/2004 | Murray et al. |
| 2004/0078077 A1 | 4/2004 | Binette et al. |
| 2004/0078090 A1 | 4/2004 | Binette et al. |
| 2004/0175408 A1 | 9/2004 | Chun et al. |
| 2004/0219182 A1 | 11/2004 | Gomes et al. |
| 2004/0236424 A1 | 11/2004 | Berez et al. |
| 2004/0249457 A1 | 12/2004 | Smith et al. |
| 2004/0267088 A1 | 12/2004 | Kammerer |
| 2004/0267362 A1 | 12/2004 | Hwang et al. |
| 2005/0002915 A1 | 1/2005 | Atala et al. |
| 2005/0038520 A1 | 2/2005 | Binette et al. |
| 2005/0048651 A1 | 3/2005 | Ryttsen et al. |
| 2005/0113937 A1 | 5/2005 | Binette et al. |
| 2005/0113938 A1 | 5/2005 | Jamiolkowski et al. |
| 2005/0125077 A1 | 6/2005 | Harmon et al. |
| 2005/0147645 A1* | 7/2005 | Budny ............ 424/423 |
| 2005/0232967 A1 | 10/2005 | Kladakis et al. |
| 2005/0234549 A1 | 10/2005 | Kladakis et al. |
| 2006/0067063 A1 | 3/2006 | Bowman |
| 2006/0084930 A1 | 4/2006 | Dhanaraj et al. |
| 2006/0204439 A1 | 9/2006 | Hellerstein |
| 2006/0223177 A1 | 10/2006 | Harris et al. |
| 2006/0280768 A1 | 12/2006 | Hwang et al. |
| 2006/0293760 A1 | 12/2006 | DeDeyne |
| 2007/0031470 A1 | 2/2007 | Kladakis et al. |
| 2007/0036767 A1 | 2/2007 | Mistry et al. |

(56) References Cited

U.S. PATENT DOCUMENTS

| | | |
|---|---|---|
| 2007/0250177 A1 | 10/2007 | Bilbo |
| 2008/0039955 A1 | 2/2008 | Hunziker |
| 2008/0071385 A1 | 3/2008 | Binette et al. |
| 2008/0226870 A1 | 9/2008 | Sypeck et al. |
| 2008/0241213 A1 | 10/2008 | Chun et al. |
| 2011/0009963 A1 | 1/2011 | Binette et al. |
| 2011/0091517 A1 | 4/2011 | Binette et al. |
| 2011/0097381 A1 | 4/2011 | Binette et al. |
| 2011/0110958 A1 | 5/2011 | Qiu et al. |
| 2011/0177134 A1 | 7/2011 | Harmon et al. |
| 2012/0156265 A1 | 6/2012 | Binette et al. |
| 2012/0165939 A1 | 6/2012 | Kladakis et al. |
| 2012/0253464 A1 | 10/2012 | Hwang et al. |
| 2013/0123937 A1 | 5/2013 | Jamiolkowski et al. |
| 2017/0049931 A1 | 2/2017 | Binette et al. |

FOREIGN PATENT DOCUMENTS

| | | |
|---|---|---|
| DE | 19812195 A1 | 9/1999 |
| EP | 0145492 A2 | 6/1985 |
| EP | 0 274 898 | 7/1988 |
| EP | 0277678 A1 | 8/1988 |
| EP | 0 411 545 A1 | 2/1991 |
| EP | 0 466 105 A2 | 1/1992 |
| EP | 0464163 A1 | 1/1992 |
| EP | 0 485 215 A1 | 5/1992 |
| EP | 0 562 864 | 9/1993 |
| EP | 0 570 331 B1 | 9/1997 |
| EP | 0955024 A2 | 11/1999 |
| EP | 1 027 897 | 8/2000 |
| EP | 1 064 958 | 1/2001 |
| EP | 1 074 270 A1 | 2/2001 |
| EP | 1 167 517 | 1/2002 |
| EP | 1177800 A1 | 2/2002 |
| EP | 1 216 717 A1 | 6/2002 |
| EP | 1216 718 | 6/2002 |
| EP | 1 348 451 | 10/2003 |
| EP | 1 410 811 | 4/2004 |
| EP | 1405649 A1 | 4/2004 |
| EP | 1 506 790 | 2/2005 |
| EP | 1537839 A1 | 6/2005 |
| EP | 1604622 A1 | 12/2005 |
| FR | 2688690 A1 | 9/1993 |
| GB | 1008193 A | 10/1965 |
| JP | 63-203154 | 8/1988 |
| JP | 63-203154 A | 8/1988 |
| JP | 02-052648 | 2/1990 |
| JP | 2143945 | 12/1990 |
| JP | 19900227442 A | 4/1992 |
| JP | 19900256824 A | 5/1992 |
| JP | 19910261753 A | 7/1993 |
| JP | 19920094329 A | 11/1993 |
| JP | 10234844 A | 9/1998 |
| JP | 11-319068 A | 11/1999 |
| JP | 19980129048 A | 11/1999 |
| JP | 19980319783 A | 5/2000 |
| JP | 2001129073 A | 5/2001 |
| JP | 2002-527402 A | 8/2002 |
| JP | 2002-535378 A | 10/2002 |
| JP | 2003320008 A | 11/2003 |
| JP | 2004008437 A | 1/2004 |
| JP | 20020165345 A | 1/2004 |
| JP | 2004-195103 | 7/2004 |
| JP | 2005-237476 A | 9/2005 |
| RU | 2187261 | 8/2002 |
| SU | 1535542 | 1/1990 |
| WO | WO 86/00533 | 1/1986 |
| WO | 9206179 A1 | 4/1992 |
| WO | 9302718 A1 | 2/1993 |
| WO | 9311805 A1 | 6/1993 |
| WO | WO 95/33821 | 12/1995 |
| WO | 9608277 A1 | 3/1996 |
| WO | WO 97/30662 | 8/1997 |
| WO | 9746665 A1 | 12/1997 |
| WO | WO 98/48860 | 11/1998 |
| WO | 9853768 A1 | 12/1998 |
| WO | 9905992 A1 | 2/1999 |
| WO | WO 99/16381 | 4/1999 |
| WO | 9939724 A1 | 8/1999 |
| WO | 9947097 A2 | 9/1999 |
| WO | 9959647 A1 | 11/1999 |
| WO | 0015248 A2 | 3/2000 |
| WO | 0016381 | 3/2000 |
| WO | 0069355 A1 | 11/2000 |
| WO | 0072782 A1 | 12/2000 |
| WO | 0074741 A2 | 12/2000 |
| WO | WO 01/15753 | 3/2001 |
| WO | 0134065 A1 | 5/2001 |
| WO | WO 01/85226 | 11/2001 |
| WO | 02/05750 A2 | 1/2002 |
| WO | 2002000272 A2 | 1/2002 |
| WO | WO 02/30324 | 4/2002 |
| WO | 02062357 A1 | 8/2002 |
| WO | 02074356 A1 | 9/2002 |
| WO | 02096268 A2 | 12/2002 |
| WO | 03/007784 A2 | 1/2003 |
| WO | 03/007786 A2 | 1/2003 |
| WO | 03/007787 A2 | 1/2003 |
| WO | 03/007788 A2 | 1/2003 |
| WO | 03/007790 A2 | 1/2003 |
| WO | 03/007805 A2 | 1/2003 |
| WO | 03/007839 A2 | 1/2003 |
| WO | 03/007847 A1 | 1/2003 |
| WO | 03007789 A2 | 1/2003 |
| WO | WO 03/017826 | 3/2003 |
| WO | 03043674 A1 | 5/2003 |
| WO | 2004012782 A1 | 2/2004 |

OTHER PUBLICATIONS

Eckersberger, M.D., Franz, "Circumferential tracheal replacement with costal cartilage", The Journal of Thoracic and Cardiovascular Surgery, 1987:94: pp. 175-180.

Matsuo, M.D., Kiyoshi et al., "Semiquantitative Correction of Posttraumatic Enophthalmos with Sliced Cartilage Grafts" Plastic and Reconstructive Surgery, vol. 83, No. 3, Postraumatic Enophthalmos, pp. 429-437.

Megumi, M.D., Yoshikazu, "Augmentation Rhinoplasty with Soft Tissue and Cartilage" Aesthetic Plastic Surgery, 1988, pp. 89-933.

Papadopulos, M.D., Angel, "Compound Implant to Projedt the Nasal Tip" Aesthetic Plastic Surgery, 1987, pp. 181-185.

Partial European Search Report, for EP 04 25 7515, dated May 9, 2005.

Powers, Dennis L. et al., "A cartilagenous graft as an adjunct to finger joint implant arthroplasty" Journal of Biomedical Materials Research, vol. 19, 1985 pp. 509-518.

Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.

Trenite, M.D., G.J. Nolst et al., "Reimplantation of autologous septal cartilage in the growing nasal septum", Rhinology, 25, 1987, pp. 225-236.

Albrecht et al., "Closure of Osteochondral Lesions Using Chondral Fragments and Fibrin Adhesive," Arch. Orthop. Trauma Surg. 101: 213-217 (1983).

Albrecht, F.H., "The Closure of Joint Cartilage Defects by Means of Cartilage Fragments and Fibrin Adhesive," Fortschr. Med. 101(37):1650-52 (1983).

Caterson EJ., et al. "Three-Dimensional Cartilage Formation by Bone Marrow-Derived Cells Seeded in Polylactide/Alginate Amalgam," *J Biomed Mater Res.* 57(3):394-403 (2001) *(Abstract Only).

Deuel, T. et al., "Growth Factors in Principles of Tissue Engineering," Second Edition, Academic Press pp. 129-141 (2000).

European Search Report, for EP 03 25 6522, dated Feb. 24, 2004.

Frenkel, S, Ph.D. and Paul E. Di Cesare, M.D., "Degradation and Repair of Articular Cartilage," *Frontiers in Bioscience*, 4th ed., pp. 671-685, pp. 1-32 (Oct. 15, 1999).

(56) References Cited

OTHER PUBLICATIONS

Gooch, K. et al., "Mechanical Forces and Growth Factors Utilized in Tissue Engineering Frontier in Tissue Engineering," *Pergamon* Chapter II.3, pp. 61-82 (1998).
Grigolo, B., et al. "Transplantation of Chondrocytes Seeded on a Hyaluronan Derivative (hyaff-11) into Cartilage Defects in Rabbits," *Biomaterials* 22(17):2417-2424 (2001) *(Abstract Only).
Hutmacher DW., "Scaffold Design and Fabrication Technologies for Engineering Tissues-State of the Art and Future Prospectives", *J Biomater Sci Polym Ed*, 12(1):107-124 (2001) *(Abstract Only).
Hutmacher DW., "Scaffolds in Tissue Engineering Bone and Cartilage", *Biomaterials*, 21(24):2529-2543 (2000) *(Abstract Only).
Ibarra, C. M.D. et al. "Tissue-Engineered Meniscus—Cells and Matrix", *Tissue Engineering in Orthopedic Surgery* 31(3):411-418 (Jul. 2000).
Koski, J. M.D. et al., "Meniscal Injury and Repair", *Orthopedic Clinics of North American*, 31(3):419-435 (Jul. 2000).
Koski, J. M.D. et al., "Tissue-Engineered Ligament—Cells, Matrix, and Growth Factors" *Tissue Engineering in Orthopedic Surgery*, 31(3):437-452 (Jul. 2000).
Murray, M., et al. "The Migration of Cells from the Ruptured Human Anterior Cruciate Ligament into Collagen-Glycosaminoglycan Regeneration Templates in Vitro," *Biomaterials* 22:2393-2402 (2001).
Radice, M. "Hyaluronan-Based Biopolymers as delivery vehicles for Bone-Marrow-Derived Mesenchymal Progenitors", *J Biomed Mater Res.* 50(2):101-9 (2000) *(Abstract Only).
Rossi, et al., "Embryonic Purkinje Cells Grafted on the Surface of the Cerebellar Cortex Integrate in the Adult Unlesioned Cerebellum," EP J. Neuroscience 4:589-93 (1992).
Sampath, T. K., et al. "In Vitro Transformation of Mesenchymal Cells Derived From Embryonic Muscle Into Cartilage in Response to Extracellular Matrix Components of Bone," *Proceedings of the National Academy of Science of the USA*, 81(1): 3419-3423 (Jun. 1984).
Schreiber RE., et al. "A Method for Tissue Engineering of cartilage by Cell Seeding on Bioresorbable Scaffolds," *Ann NY Acad Sci.* 875:394-404 (1999) *(Abstract Only).
Stone, K. et al. "Meniscal Regeneration with Copolymeric Collagen Scaffolds," *American Journal of Sports Medicine* 20(2):104-111 (1992).
Van Susante JLC, et al. "Linkage of Chondroitin-Sulfate to Type I Collagen Scaffolds Stimulates the Bioactivity of Seeded Chondrocytes in Vitro", *Biomaterials* 22(17):2359-2369 (2001) *(Abstract Only).
Japanese Office Action dated Aug. 28, 2012 for Application No. 2004-233655 (6 Pages).
Takeuchi et al., The present situation and vision of joint transplantation. Journal of Clinical and Experimental Medicine. 1995;164(10):748-9. Translation.
Andreasen et al., Evaluation of different types of autotransplanted connective tissues as potential periodontal ligamant substitues: An experimental replantation study in monkeys. International Journal of Oral Surgery, Jun. 1981, vol. 10, Issue 3, pp. 189-201.
Japanese Office Action dated Dec. 6, 2011 for Application No. 2004-233655 (8 Pages).
Australian Search Report for AU application No. 2006200194, dated Feb. 4, 2008.
Dialog English language abstract for DE 19812195.
Examination file history of EP 01310810.
www.btc-bti.com/applications/cryogenicstorage.htm, 6 pgs, printed Jan. 11, 2010.
www.bio-medicine.org/medicine-technology-1/New-Study-Shows-Cloning-From-Dried-Cells-Now-Possible-2988-1/, 2 pgs, printed Jan. 11, 2010.
Japanese Office Action, from JP 2004-191861, dated Mar. 1, 2011.
Andreasen, J.O. et al. Evaluation of different types of autotransplanted connective tissues as potential periodontal ligamant substitues: An experimental replantation study in monkeys, International Journal of Oral Surgery, Jun. 1981, vol. 10, Issue 3, pp. 189-201 (Abstract only).
European Search Report for EP 10075307 dated Oct. 6, 2010.
Chen G., Ushida T., and Tateishi T., "A hybrid network of synthetic polymer mesh and collagen sponge," Chem. Commun., 2000, pp. 1505-1506.
European Search Report for EP 08075114.2, dated May 12, 2010.
Heller: "Handbook of Biodegradable Polymers," 1997, Hardwood Academic Press, pp. 99-118.
Solov'ev et al., "Functional Activity of Hepatocytes in Liver Fragments In Vitro as a Function if Fragment Size and Duration of Culturing" Bull Exp Biol Med. Jun. 2000;129(6):595-7.
Boland et. al., J. Macromol. Sci.-Pure Appl. Chem., 2001, A38(12), p. 1231-1243).
Buschmann et al., J. Orthop. Res. 1992; 10:745-752.
De Groot, J.H. et al., "Meniscal tissue regeneration in porous 50/50 copoly(l-lactide/epsilon-caprolactone) implants" Biomaterials, vol. 18, No. 8, 1997, pp. 613-622.
De Groot, J.H. et al., "Use of porous polyurethanes for meniscal reconstruction and meniscal prostheses" Biomaterials, vol. 17, No. 2, 1996, pp. 163-173.
European Search Report, for EP Application No. 07252617.1, dated Nov. 2, 2007.
Young, A.T., "Microcellular Foams via Phase Separation," J. Vac. Sci. Technolol., vol. 4(3), May/Jun. 1986.
Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.
Tienen T. G. et al., "A porous polymer scaffold for meniscal lesion repair-A study in dogs" Biomaterials, vol. 24, No. 14, 2003, pp. 2541-2548.
Nioshiki Y., "A new trend in hybrid artificial organs" J. Artificial Organs, 1999, vol. 2: pp. 93-96.
Tozum et al., J Canadian Dental Assoc. Nov. 2003. 69(10):664-664h.
Kemnitzer and Kohn, in the Handbook of Biodegradable Polymers, edited by Domb, et. al., Hardwood Academic Press, pp. 251-272 (1997).
Journal of Biomaterials Research, vol. 22, pp. 993-1009, 1988 by Cohn and Younes.
Cohn, Polymer Preprints (ACS Division of Polymer Chemistry), vol. 30(1), p. 498, 1989.
Allcock in the Encyclopedia of Polymer Science, vol. 13, pp. 31-41, Wiley Intersciences, John Wiley & Sons, 1988.
Vandorpe, et al in the Handbook of Biodegradable Polymers, edited by Domb, et al., Hardwood Academic Press, pp. 161-182 (1997).
Kurashina, K. et al. "Osteogenesis in muscle with composite graft of hydroxyapatite and autogenous calvarial periosteum: a preliminary report" Biomaterials (1995) vol. 16, No. 2, pp. 119-123.
Ikada, Yoshito, Handbook of Fiber Science and Technology, Edited by Menachem Lewin, Jack Preston, vol. III, Part B, Chapters, pp. 253, 289-295, Published by M. Dekker, 1983.
(7th Edition, 1999).
Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.
Dialog English language abstract for DE 19812195, published Sep. 30, 1999.
Japanese Office Action dated Apr. 24, 2012 for Application No. 2007-171032 (6 Pages).
Japanese Office Action dated Feb. 26, 2013 for Application No. 2007-171032 (4 Pages).
Lobler et al., Biomaterial implants induce the inflammation marker CPR at the site of implantation, Journal of Biomedical Materials Research, 2002, vol. 61, No. 1, pp. 165-167.
Guy Fortier, Development of Biosensors Based on Immobilization of Enzymes in Eastman AQ Polymer Coated with a Layer of Nation, Analytical Letters, vol. 23 No. 9, Sep. 1990. Abstract.
European Search Report for Application No. 05256123, dated Feb. 1, 2006.
European Search Report for Application No. 04251265.7 dated Jul. 9, 2004.

(56) References Cited

OTHER PUBLICATIONS

[No author listed] Warm Glass Disclosure "The Basic Fusing and Slumping Process." 1999. Retrieved from the internet Nov. 22, 2005, 5 pages.
O'Driscoll S.W. et al., "Viability of Periosteal Tissue Obtained Postmortem," Cell Transplantation, 1999, col. 8, pp. 611-616.
Bruns J. et al., "The in vitro influence of different culture conditions on the potential of sheep rib perichondrium to form hyaline-like cartilage: Evaluation of glueing materials used for in vivo graft fixation," Virchows Archiv., 1994, vol. 424, pp. 169-175.

* cited by examiner

CONTROL

80a

SCAFFOLD + BMT 82b  84b

SCAFFOLD + BMT + PRP 84c  82c

SCAFFOLD + FPV + BMT + PRP 80d  82d
84d

SCAFFOLD + PV + BCT + PRP

PRP stimulates cell migration into bioresorbable scaffolds

CDMP-1 stimulates cell migration into bioresorbable scaffolds

CONTROL

150ng CDMP-1

SCAFFOLDS WITH VIABLE TISSUE

FIELD OF THE INVENTION

The present invention relates to methods and devices for repairing and replacing torn or damaged tissue, and in particular to tissue implants having viable tissue capable of tissue regeneration and integration with tissue surrounding the area to be repaired, as well as methods for using such tissue implants.

BACKGROUND OF THE INVENTION

Injuries to tissue, such as cartilage, skin, muscle, bone, tendon, and ligament where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques. Despite these conventional methods of tissue repair, there continues to be a need for surgical solutions that facilitate the regeneration of new, healthy tissue to provide more reliable repair and healing of the injured or damaged tissue over the long term.

The search for a reliable source of viable cells for tissue regeneration has been pursued for years. Recent tissue engineering techniques for repairing tissue have typically involved replacing or reconstructing damaged or injured tissue with cells that have been manipulated ex vivo to stimulate new tissue growth. The cells are usually incorporated into a delivery vehicle (e.g., a scaffold or surgical implant) for placement at the tissue site, whereupon new tissue can be grown. Various surgical implants are known and have been used in surgical procedures to help achieve these benefits. For example, it is known to use various devices and techniques for creating implants having isolated cells loaded onto a delivery vehicle. Such cell-seeded implants have been used in an in vitro method of making and/or repairing cartilage by growing cartilaginous structures that consist of chondrocytes seeded onto biodegradable, biocompatible fibrous polymeric matrices as well as matrices developed from collageneous materials. Such methods require the initial isolation of chondrocytes from cartilaginous tissue prior to the chondrocytes being seeded onto the polymeric matrices. Other techniques for repairing damaged tissue employ implants having stem or progenitor cells that are used to produce the desired tissue. For example, it is known to use stem or progenitor cells, such as the cells within fatty tissue, muscle, bone marrow, or embryonic tissue to regenerate bone, cartilage, and other soft tissues in a patient. For example, stem cells from fat are removed from the patient and placed in an environment favorable to cartilage formation, thereby inducing the cells to proliferate and to create a different type of cell, such as cartilage cells.

While the trend towards using tissue engineering approaches to tissue repair continues to gain popularity, mainly because of the long-term benefits provided to the patient, these current techniques are not without drawbacks. One disadvantage with current tissue engineering techniques is that they can be time consuming. A typical process involves the harvest of a tissue sample from the patient in a first surgical procedure, which is then transported to a laboratory for cell isolation, culture and amplification. The cell sample is grown for a period of 3 to 4 weeks using standard cell culture techniques to create a cell bank. Once the cell population has reached a target number, the cells are sent back to the surgeon for implantation during a second surgical procedure. This manual, labor-intensive process is extremely costly and time consuming. Although the clinical data suggest long-term benefits for the patient, the prohibitive cost of the procedure, combined with the traumatic impact of two surgical procedures, has hampered adoption of these techniques. And though allografts have been used for tissue repair in the past, this solution is also not ideal because of the limited availability of graft material and the potential for disease transmission.

For these reasons, there continues to exist a need in this art for novel devices and methods for regenerating tissue which are less time consuming and easier to implement. It is also desirable to provide an implant which can serve as a reliable source of viable cells, and which can be made in a quick and efficient manner for immediate use during surgery. There is thus a need for a less costly solution to repairing tissue defects or injuries that also provides the advantages of tissue regeneration, without the encumbrances of the currently available devices and methods of tissue repair previously mentioned.

SUMMARY OF THE INVENTION

The present invention generally provides a composite implant for repairing a tissue defect in a patient. In one embodiment, the implant is a porous tissue scaffold having at least one pocket formed therein and adapted to contain a viable tissue. The tissue scaffold can have a variety of shapes and configurations, and in one embodiment it includes top and bottom portions. The top and bottom portions can be at least partially mated to one another, and in an exemplary embodiment they are heat sealed to one another around a perimeter thereof to form an enclosed pocket therebetween. Heat sealing can be performed either before or after the viable tissue is loaded into the scaffold. In another embodiment, the tissue scaffold is substantially wedge-shaped and the pocket comprises a hollow interior formed in the tissue scaffold, and/or at least one lumen extending into the tissue scaffold. The tissue scaffold can also optionally include at least one surface feature formed thereon to promote blood vessel formation. By way of non-limiting example, the surface feature can be in the form of a plurality of channels formed on an outer surface of the tissue scaffold.

In a further embodiment of the present invention, the tissue scaffold can include a viable tissue disposed within the pocket. The viable tissue should be effective to migrate into the scaffold to integrate with native tissue surrounding the scaffold. At least one bioactive substance can be applied to the viable tissue to stimulate cell growth. Suitable bioactive substances include, for example, blood clots, platelet rich plasma, cartilage-derived morphogenic proteins, recombinant human growth factors, and combinations thereof. In another embodiment, the bioactive substance can additionally or alternatively be applied to the tissue scaffold.

The present invention also provides a method for repairing defective tissue that includes the steps of providing a tissue scaffold having at least one pocket formed therein and adapted to contain a viable tissue, obtaining a viable tissue, loading the viable tissue into the at least one pocket of the tissue scaffold, and implanting the tissue scaffold with the viable tissue disposed therein at a defect site in a patient's body. The method can also include the step of applying at least one bioactive substance to the viable tissue to stimulate cell growth.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides a composite implant that includes a tissue scaffold having at least one pocket formed therein, and a viable tissue disposed within the pocket of the tissue scaffold. The use of a pocket is particularly advantageous in that it helps retain viable tissue within the composite implant and it minimizes the loss of viable tissue following placement at a defect site in a patient. The pocket is also advantageous in that the viable tissue can migrate and populate the scaffold, thereby enhancing the integration between the native tissue and the composite implant.

A person skilled in the art will appreciate that the biocompatible composite implants of the present invention can be used in the treatment of various types of tissue for various purposes, including but not limited to tissue repair, tissue bulking, cosmetic treatments, therapeutic treatments, tissue remodeling or augmentation, and tissue sealing. In an exemplary embodiment, the implants are used for the repair and/or regeneration of diseased or damaged tissue.

The tissue scaffold used to form the composite implant of the present invention can have various configurations, shapes, and sizes. FIGS. 1-7 illustrate a variety of exemplary composite implants, each formed from a tissue scaffold having at least one pocket formed therein containing a viable tissue. As stated above, the pocket allows the viable tissue to grow into and through the scaffold, such that the tissue becomes embedded in and integrated with the scaffold.

Figure 1:
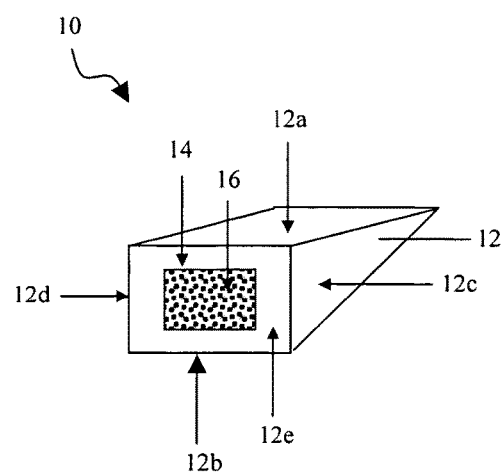
FIG. 1 is a perspective view of one embodiment of a composite implant in accordance with the present invention.
Figure 2:
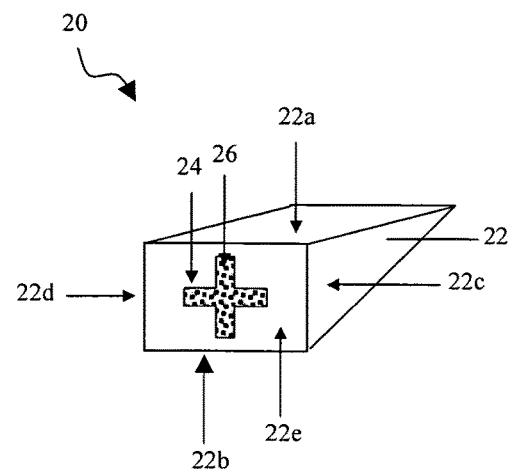
FIG. 2 is a perspective view of another embodiment of a composite implant in accordance with the present invention.

In FIGS. 1 and 2, the composite implant 10, 20 is formed from a tissue scaffold 12, 14 that is substantially wedge-shaped, and in particular that includes opposed top and bottom walls 12a, 12b, 22a, 22b, opposed side walls 12c, 12d, 22c, 22d extending between the top and bottom walls 12a, 12b, 22a, 22b, and an end wall 12e, 22e that connects the top, bottom, and opposed side walls 12a, 12b, 12c, 12d, 22a, 22b, 22c, 22d. The pocket 14, 24 in each scaffold 12, 22 is formed as a lumen that extends into the end wall 12e, 22e of each scaffold 12, 22. While the opening of the pocket 14, 24 can be formed in any wall of the implant 10, 20, an end wall 12e, 22e opening is particularly advantageous in that it simplifies loading of the implant with the viable tissue 16, 26. Moreover, when the composite implant 10, 20 is implanted, native tissue surrounding the scaffold 12, 22 will abut the pocket opening to help maintain the viable tissue 16, 26 therein.

Still referring to FIGS. 1 and 2, while the pocket 14, 24 in each implant 10, 20 can have virtually any shape and size, the opening of the pocket 14 shown in FIG. 1 is substantially rectangular in shape, and the opening of the pocket 24 shown in FIG. 2 is in the form of a cruciform. Each pocket is preferably substantially centrally located in the end wall 12e, 22e of the scaffold 12, 22, as shown, and each pocket preferably extends through a substantial portion of the scaffold 12, 22. This construction facilitates migration of the viable tissue through the entire scaffold 12, 22 in all directions.

Figure 3:
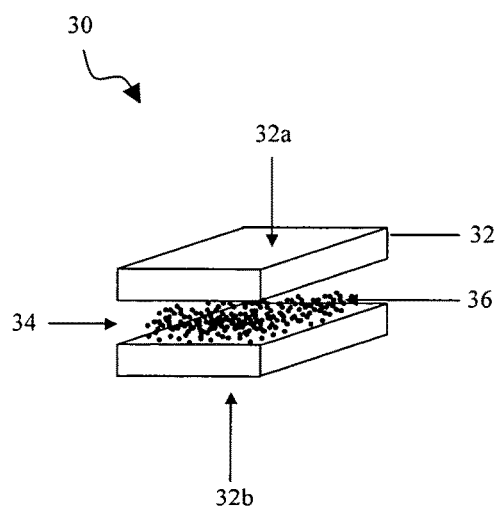
FIG. 3 is a perspective view of a composite implant in accordance with another embodiment the present invention.

FIG. 3 illustrates another embodiment of a composite implant 30. In this embodiment, the tissue scaffold 32 includes upper and lower portions or layers 32a, 32b that are configured to sandwich a viable tissue 36 in a pocket 34 formed therebetween. The viable tissue 36 can merely be placed on one or the layers, e.g., lower layer 32b, and the upper layer 32a can then be positioned thereon to form the composite implant. A person skilled in the art will appreciate that while the illustrated layers 32a, 32b are substantially rectangular, each layer can have virtually any shape and size.

Figure 4:
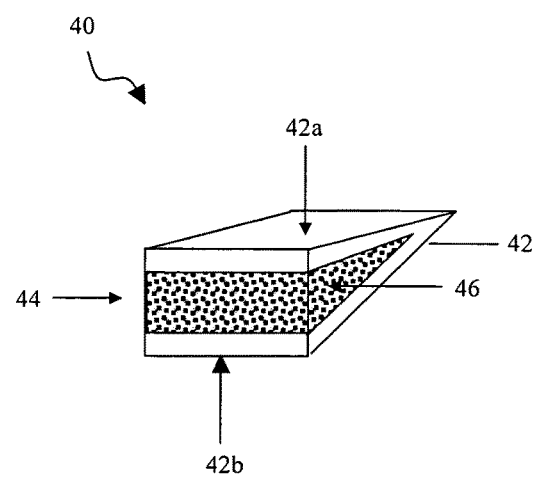
FIG. 4 is a perspective view of yet another embodiment of a composite implant in accordance with the present invention.

FIG. 4 illustrates yet another embodiment of a composite implant 40 having a tissue scaffold 42 that includes upper and lower layers 42a, 42b with a viable tissue 46 disposed in a pocket 44 formed therebetween. The upper and lower layers 42a, 42b are mated to one another at only one end thereof. Thus, while the scaffold 42 is substantially wedge shaped, it does not include sidewalls that are mated to one another as shown in FIGS. 1 and 2.

Figure 5A:
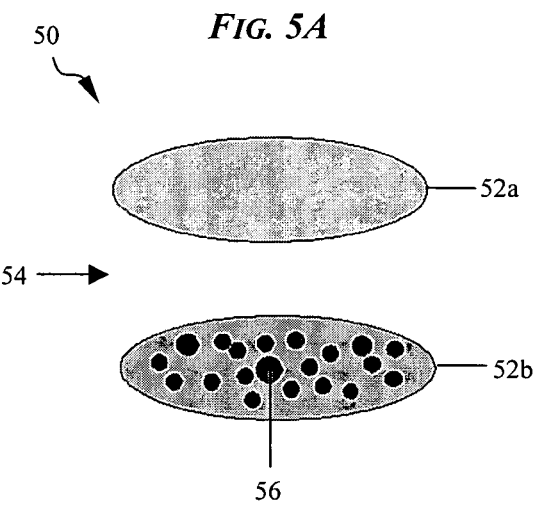
FIG. 5A is an illustration of a composite implant having a top portion and a bottom portion with a viable tissue disposed thereon in accordance with another embodiment of the present invention.
Figure 5B:
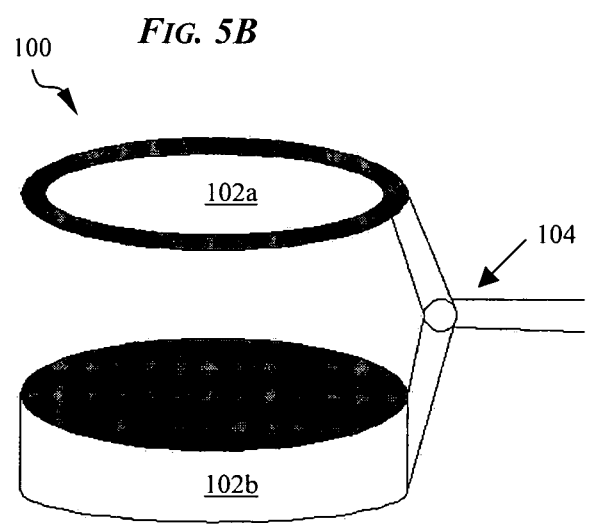
FIG. 5B is an illustration of a heat sealing apparatus in accordance with the present invention.
Figure 5C:
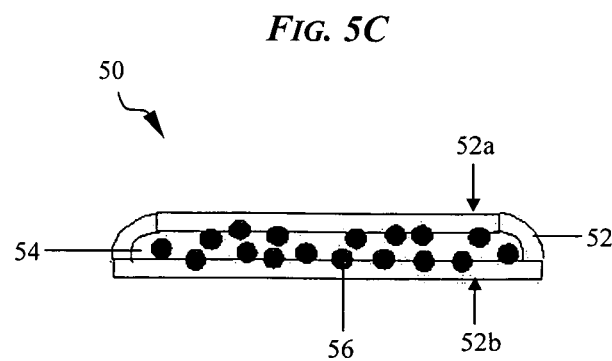
FIG. 5C illustrates the composite implant of FIG. 5A after being sealed using the heat sealing apparatus of FIG. 5B.

In another embodiment of the present invention, one or more edges of the tissue scaffold can be at least partially sealed to one another to form the pocket which is adapted to contain a viable tissue. By way of non-limiting example, FIGS. 5A and 5C illustrate a composite implant 50 formed from a tissue scaffold 52 having top and bottom layers 52a, 52b that are sealed to one another around a perimeter thereof to retain a viable tissue 56 disposed therebetween. While virtually any technique can be used to mate the layers 52a, 52b to one another, in an exemplary embodiment the layers 52a, 52b are heat sealed to one another. Heat sealing can be performed before or after the viable tissue 56 is placed between the layers 52a, 52b, however care should be taken to avoid damage to the viable tissue 56. By way of non-limiting example, FIG. 5B illustrates a heat sealing apparatus 100 that includes a lower member or tray 102b that is effective to seat the layers 52a, 52b with the viable tissue 56 disposed therebetween. The heat sealing apparatus 100 also includes an upper member 102a that is preferably connected to the lower member 102b by a lever or hinge 104, and that is effective to apply heat to the perimeter of the tissue scaffold 52 to seal the layers 52a, 52b to one another to form the composite implant 50 shown in FIG. 5C. In use, the heat sealed scaffold is particularly advantageous in that it prevents the viable tissue from migrating from the scaffold, and it can also be used to provide mechanical reinforcement to the implant for receiving a suture or other attachment mechanism for securing the implant to surrounding tissue. A person skilled in the art will appreciate that a variety of techniques can be used to mate the layers to one another including, for example, adhesive, sutures, a fold or roll seal, a mechanical press seal, etc.

Figure 6:
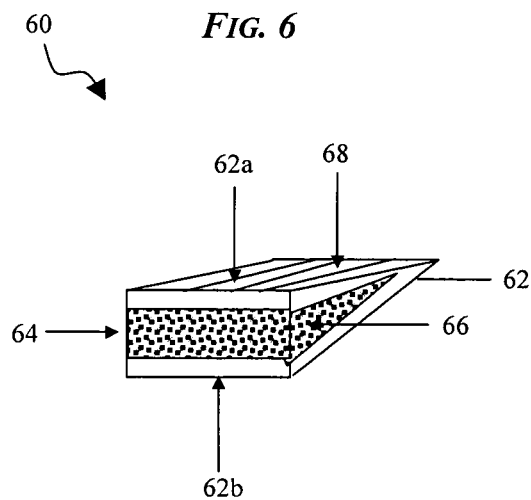
FIG. 6 is a perspective view of yet another embodiment of a composite implant having surface features formed thereon according to another embodiment of the present invention.
Figure 7:
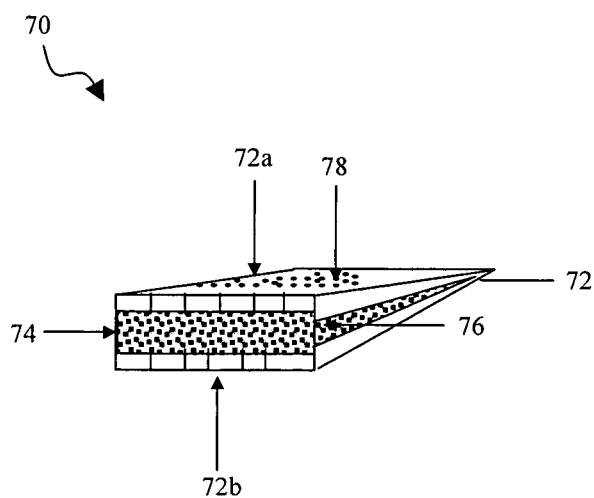
FIG. 7 illustrates another embodiment of a composite implant having surface features formed thereon.

In other embodiments of the present invention, the composite implant can include one or more surface features formed on the tissue scaffold to promote and/or guide blood vessel formation. FIGS. 6 and 7 illustrate exemplary implants 60, 70 with surface features formed thereon. As shown, each implant 60, 70 generally includes a tissue scaffold 62, 72 formed from top and bottom portions 62a, 62b, 72a, 72b that at mated to one another at one end thereof such that each implant 60, 70 is substantially wedge-shaped. A viable tissue 66, 76 is disposed within the pocket 64, 74 that is formed between the top and bottom portions 62a, 62b, 72a, 72b. In the embodiment illustrated in FIG. 6, the surface features are formed on the top and bottom layers 62a, 62b, and they are in the form of channels 68 that extend there across and that are spaced apart from one another. In the embodiment illustrated in FIG. 7, the surface features are also formed on the top and bottom layers 72a, 72b, however they are in the form of bores 78 formed therein. A person skilled in the art will appreciate that the location and quantity of surface features can vary.

The materials used to form the composite implant of the present invention can also vary, and a variety of materials and techniques for forming a tissue scaffold are known in the art and can be used with the present invention. In an exemplary embodiment, however, the tissue scaffold is formed using a material or delivery vehicle that is biocompatible and that has sufficient structural integrity and physical and/or mechanical properties to effectively provide for ease of handling in an operating room environment. Sufficient strength and physical properties can be developed in the scaffold through the selection of materials used to form the scaffold, and the manufacturing process. In addition, the scaffold is preferably sufficiently porous to allow cell growth therein. Preferably, the median pore size is in the range of about 100 to 500 microns. The scaffold can also optionally be sufficiently pliable to allow the scaffold to adjust to the dimensions of the target site of implantation, and/or to accommodate tissue growth within the interior region of the scaffold, so that the geometry of the scaffold can be remodeled as tissue ingrowth increases.

In an exemplary embodiment, the scaffold is formed from a bioresorbable or bioabsorbable material, and more preferably from a bioresorbable or bioabsorbable material that has the ability to resorb in a timely fashion in the body environment. The differences in the absorption time under in vivo conditions can also be the basis for combining two different copolymers when forming the scaffolds of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible scaffold. Depending upon the processing technique used, the two constituents can be either randomly inter-connected bicontinuous phases, or the constituents could have a gradient-like architecture in the form of a laminate-type composite with a well integrated interface between the two constituent layers. The microstructure of these scaffolds can be optimized to regenerate or repair the desired anatomical features of the tissue that is being regrown.

In one embodiment of the present invention, the scaffold can be formed from a biocompatible polymer. A variety of biocompatible polymers can be used to make the biocompatible tissue implants or scaffold devices according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring.

In embodiments where the scaffold includes at least one synthetic polymer, suitable biocompatible synthetic polymers can include polymers selected from the group consisting of aliphatic polyesters, poly(amino acids), copoly(etheresters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-,L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; α-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,αdiethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Other useful polymers include polyphosphazenes, co-, ter- and higher order mixed monomer based polymers made from L-lactide, D,L-lactide, lactic acid, glycolide, glycolic acid, para-dioxanone, trimethylene carbonate and ε-caprolactone.

In embodiments where the scaffold includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of non-limiting example, the biocompatible scaffold can be constructed from a collagen-based small intestine submucosa.

In still yet another embodiment, the preferred scaffold for tissue repair, including cartilage, meniscus, tendon, ligament, and skin repair, is constructed from a naturally occurring extracellular matrix material ("ECM"), such as that found in the stomach, bladder, alimentary, respiratory, urinary, integumentary, genital tracts, or liver basement membrane of animals. Preferably, the ECM is derived from the alimentary tract of mammals, such as cows, sheeps, dogs, cats, and most preferably from the intestinal tract of pigs. The ECM is preferably small intestine submucosa ("SIS"), which can include the tunica submucosa, along with basilar portions of the tunica mucosa, particularly the lamina muscularis mucosa and the stratum compactum.

For the purposes of this invention, it is within the definition of a naturally occurring ECM to clean and/or comminute the ECM, or even to cross-link the collagen fibers within the ECM. Also, while reference is made to SIS, it is understood that other naturally occurring ECMs are within the scope of this invention. Thus, as used herein, the terms "naturally occurring extracellular matrix" or "naturally occurring ECM" can refer to extracellular matrix material that has been cleaned, disinfected, sterilized, and optionally cross-linked.

Where SIS is used, an SIS graft can be harvested in a variety of ways, as will be understood by one skilled in the art. The resulting graft material can have a variety of geometries and consistencies including for example, coiled, helical, spring-like, randomized, branched, sheet-like, tubular, spherical, fragmented, fluidized, comminuted, liquefied, foamed, suspended, gel-like, injectable, powdered, ground, and sheared.

In yet another embodiment of the present invention, the scaffold can be formed using tissue grafts, such as may be obtained from autogeneic tissue, allogeneic tissue and xenogeneic tissue. By way of non-limiting example, tissues such as skin, cartilage, ligament, tendon, periosteum, perichondrium, synovium, fascia, mesenter and sinew can be used as tissue grafts to form the biocompatible scaffold. In some embodiments where an allogeneic tissue is used, tissue from a fetus or newborns can be used to avoid the immunogenicity associated with some adult tissues.

In other embodiments of the present invention, the tissue scaffold can be formed from elastomeric copolymers such as, for example, polymers having an inherent viscosity in the range of about 1.2 dL/g to 4 dL/g, more preferably about 1.2 dL/g to 2 dL/g, and most preferably about 1.4 dL/g to 2 dL/g as determined at 25° C. in a 0.1 gram per deciliter (g/dL) solution of polymer in hexafluoroisopropanol (HFIP). Suitable elastomers also preferably exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, the elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers include, but are not limited to, elastomeric copolymers of ε-caprolactone and glycolide with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 95:5 to about 30:70 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Other examples of suitable biocompatible elastomers are described in U.S. Pat. No. 5,468,253.

In another embodiment of the present invention, the tissue scaffold can be formed from an elastomer that is a copolymer of 35:65 ε-caprolactone and glycolide, formed in a dioxane solvent and including a polydioxanone mesh. In another embodiment, the elastomer used to form the tissue scaffold can be a copolymer of 40:60 ε-caprolactone and lactide with a polydioxanone mesh. In yet another embodiment, the elastomer is a 50:50 blend of a 35:65 copolymer of ε-caprolactone and glycolide and 40:60 copolymer of ε-caprolactone and lactide. The polydioxanone mesh may be in the form of a one layer thick two-dimensional mesh or a multi-layer thick three-dimensional mesh.

In another embodiment of the present invention, the tissue scaffold can be formed from a biocompatible ceramic material. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

In yet another embodiment of the present invention, the scaffold can be formed from a polymeric foam component having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. The polymeric foam component can, optionally, contain a reinforcing component, such as for example, the textiles disclosed above. In some embodiments where the polymeric foam component contains a reinforcing component, the foam component can be integrated with the reinforcing component such that the pores of the foam component penetrate the mesh of the reinforcing component and interlock with the reinforcing component.

It may also be desirable to use polymer blends to form scaffolds which transition from one composition to another composition in a gradient-like architecture. Scaffolds having this gradient-like architecture are particularly advantageous in tissue engineering applications to repair or regenerate the structure of naturally occurring tissue such as cartilage (articular, meniscal, septal, tracheal, auricular, costal, etc.), tendon, ligament, nerve, esophagus, skin, bone, and vascular tissue. For example, by blending an elastomer of ε-caprolactone-co-glycolide with E-caprolactone-co-lactide (e.g., with a mole ratio of about 5:95) a scaffold may be formed that transitions from a softer spongy material to a stiffer more rigid material, for example, in a manner similar to the transition from cartilage to bone. Clearly, one skilled in the art will appreciate that other polymer blends may be used for similar gradient effects, or to provide different gradients (e.g., different absorption profiles, stress response profiles, or different degrees of elasticity).

One of ordinary skill in the art will appreciate that the selection of a suitable material for forming the biocompatible scaffold of the present invention depends on several factors. These factors include in vivo mechanical performance; cell response to the material in terms of cell attachment, proliferation, migration and differentiation; biocompatibility; and optionally, bioabsorption (or biodegradation) kinetics. Other relevant factors include the chemical composition, spatial distribution of the constituents, the molecular weight of the polymer, and the degree of crystallinity.

The tissue scaffold used to form the composite implant can also include a reinforcing material comprised of any absorbable or non-absorbable textile having, for example, woven, knitted, warped knitted (i.e., lace-like), non-woven, and braided structures. In one embodiment, the reinforcing material has a mesh-like structure. In any of the above structures, mechanical properties of the material can be altered by changing the density or texture of the material, the type of knit or weave of the material, the thickness of the material, or by embedding particles in the material. The mechanical properties of the material may also be altered by creating sites within the mesh where the fibers are physically bonded with each other or physically bonded with another agent, such as, for example, an adhesive or a polymer.

The fibers used to make the reinforcing component can include monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one embodiment, the fibers are formed from 95:5 copolymer of lactide and glycolide.

In another embodiment, the fibers that form the reinforcing material can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

The biocompatible scaffolds as well as the reinforcing material may also be formed from a thin, perforation-containing elastomeric sheet with pores or perforations to allow tissue ingrowth. Such a sheet could be made of blends or copolymers of polylactic acid (PLA), polyglycolic acid (PGA), polycaprolactone (PCL), and polydioxanone (PDO).

A person skilled in the art will appreciate that one or more layers of the reinforcing material may be used to reinforce the composite implant of the invention. In addition, biodegradable textile scaffolds, such as, for example, meshes, of the same structure and chemistry or different structures and chemistries can be overlaid on top of one another to fabricate biocompatible tissue implants with superior mechanical strength.

The source of viable tissue can also vary, and the tissue can have a variety of configurations. In one embodiment, however, the tissue is in the form of finely minced tissue fragments, which enhance the effectiveness of the regrowth and healing response. In another embodiment, the viable tissue can be in the form of a tissue slice or strip that harvested from healthy tissue that contains viable cells capable of tissue regeneration and/or remodeling, as described in U.S. patent application Ser. No. 10/729,046 filed Dec. 5, 2003 and entitled "Viable Tissue Repair Implants and Methods of Use." The tissue slice is preferably harvested to have a geometry that is suitable for implantation at the site of the injury or defect, and the harvested tissue slice is preferably dimensioned to allow the viable cells contained within the tissue slice to migrate out and proliferate and integrate with tissue surrounding the repair site.

Suitable tissue that can be used to obtain viable tissue includes, for example, cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood, and combinations thereof. The tissue used to construct the tissue implant can be autogeneic tissue, allogeneic tissue, or xenogeneic tissue.

The particle size of each tissue fragment can also vary. By way of non-limiting example, the tissue size can be in the range of about 0.1 and 3 mm$^3$, in the range of about 0.5 and 1 mm$^3$, in the range of about 1 to 2 mm$^3$, or in the range of about 2 to 3 mm$^3$, but preferably the tissue particle is less than 1 mm$^3$.

The viable tissue can also optionally be combined with a variety of other materials, including carriers, such as a gel-like carrier or an adhesive. By way of non-limiting example, the gel-like carrier can be a biological or synthetic hydrogel such as hyaluronic acid, fibrin glue, fibrin clot, collagen gel, collagen-based adhesive, alginate gel, cross-linked alginate, chitosan, synthetic acrylate-based gels, platelet rich plasma (PRP), platelet poor plasma (PPP), PRP clot, PPP clot, blood, blood clot, blood component, blood component clot, Matrigel, agarose, chitin, chitosan, polysaccharides, poly(oxyalkylene), a copolymer of poly(ethylene oxide)-poly(propylene oxide), poly(vinyl alcohol), laminin, elasti, proteoglycans, solubilized basement membrane, or combinations thereof. Suitable adhesives include, but are not limited to, hyaluronic acid, fibrin glue, fibrin clot, collagen gel, collagen-based adhesive, alginate gel, cross-linked alginate, gelatin-resorcin-formalin-based adhesive, mussel-based adhesive, dihydroxyphenylalanine (DOPA)-based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), PRP clot, PPP clot, blood, blood clot, blood component, blood component clot, polyethylene glycol-based adhesive, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

The viable tissue can also be contacted with a matrix-digesting enzyme to facilitate tissue migration out of the extracellular matrix surrounding the viable tissue. The enzymes can be used to increase the rate of cell migration out of the extracellular matrix and into the tissue defect or injury, or scaffold material. Suitable matrix-digesting enzymes that can be used in the present invention include, but are not limited to, collagenase, chondroitinase, trypsin, elastase, hyaluronidase, peptidase, thermolysin, matrix metalloproteinase, gelatinase and protease. Preferably, the concentration of minced tissue particles in the gel-carrier is in the range of approximately 1 to 1000 mg/cm$^3$, and more preferably in the range of about 1 to 200 mg/cm$^3$.

Other viable tissue sources and methods for preparing viable tissues are disclosed in U.S. patent application Ser. No. 10/723,982 entitled "Conformable Tissue Repair Implant Capable Of Injection Delivery," filed on Nov. 26, 2003 and incorporated by referenced herein in its entirety.

In use, the composite implant is preferably prepared by obtaining a viable tissue, preparing the tissue if necessary, and loading the tissue into the pocket(s) in the tissue scaffold. The tissue used to obtain viable tissue sample can vary. In an exemplary embodiment, however, the viable tissue is obtained from or includes finely minced tissue fragments which enhance the effectiveness of the regrowth and healing response. The minced tissue fragments can be obtained using any of a variety of conventional techniques, such as for example, by biopsy or other surgical removal. Preferably, the tissue sample is obtained during the repair surgery to minimize the total number of surgeries performed on the patient. Once a sample of living tissue has been obtained, the sample can then be processed under sterile conditions to create a suspension having at least one minced, or finely divided tissue particle. A carrier, such as a gel-like carrier or an adhesive, can optionally be used to form the suspension. It is also possible to harvest the tissue in minced form such that further processing is not necessary.

Once the viable tissue is prepared, the scaffold is loaded, and optionally sealed if necessary. The composite can then be implanted and retained at the defect site by the force of compression against the tissue implant by the surrounding tissue. For instance, the tissue implant can be dimensioned to have a slightly larger overall size than the area of the defect so that, upon implantation, the tissue implant can form a tight, interference fit within the defect. Alternatively, the tissue implant can be secured to the defect using any conventional method such as with a retaining element or an adhesive. The retaining element can be, for example, a fastener, staple, tissue tack, suture, adhesive, or any combination of these. One skilled in the art will appreciate that a variety of techniques can be used to attach the tissue implant to the surrounding tissue.

In another embodiment of the present invention, a bioactive agent may be incorporated within and/or applied to the tissue scaffolds, and/or it can be applied to the viable tissue. Preferably, the bioactive agent is incorporated within, or coated on, the scaffold prior to the addition of viable tissue to the scaffold. The bioactive agent(s) can be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED® and SURGICEL®, available from Ethicon, Inc.), hyaluronic acid, and compounds or agents that suppress the immune system (e.g., immunosuppressants).

By way of non-limiting example, other types of effectors present within the implant of the present invention can include heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the scaffold, or alternatively, the scaffold can include a source of growth factors, such as for example, platelets. "Bioactive agents," as used herein, can include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF-β I-III), parathyroid hormone, parathyroid hormone related peptide, bone morphogenic proteins (e.g., BMP-2, BMP-4; BMP-6; BMP-12), sonic hedgehog, growth differentiation factors (e.g., GDF5, GDF6, GDF8), recombinant human growth factors (e.g., MP52), cartilage-derived morphogenic proteins (CDMP-1)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopaedic field, it is anticipated that at least some of these substances will have use in the present invention, and such substances should be included in the meaning of "bioactive agent" and "bioactive agents" unless expressly limited otherwise.

Biologically derived agents, suitable for use as effectors, include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also appropriate biologically derived agents. If other such substances have therapeutic value in the orthopaedic field, it is anticipated that at least some of these substances will have use in the present invention, and such substances should be included in the meaning of "biologically derived agent" and "biologically derived agents" unless expressly limited otherwise.

Biologically derived agents also include bioremodelable collageneous tissue matrices. The terms "bioremodelable collageneous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, whatever the source. Although the term "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The tissue scaffolds of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited.

Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins).

This cellular messenger can be an antibody (e.g., secreted from plasma cells), a hormone, (e.g., a paracrine, autocrine, or exocrine hormone), a cytokine, or natural or synthetic fragments thereof.

The tissue implants of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold of the tissue repair implant, the implant can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One of ordinary skill in the art will appreciate that the identity of the bioactive agent may be determined by a surgeon, based on principles of medical science and the applicable treatment objectives. It is understood that the bioactive agent or effector of the tissue repair implant can be incorporated within the tissue scaffold before or after manufacture of the tissue scaffold, or before or after the surgical placement of the implant.

Prior to surgical placement, the tissue scaffold can be placed in a suitable container comprising the bioactive agent. After an appropriate time and under suitable conditions, the scaffold will become impregnated with the bioactive agent. Alternatively, the bioactive agent can be incorporated within the scaffold by, for example, using an appropriately gauged syringe to inject the biological agent(s) into the scaffold. Other methods well known to those of skilled in the art can be applied in order to load a scaffold with an appropriate bioactive agent, such as mixing, pressing, spreading, centrifuging and placing the bioactive agent into the scaffold. Alternatively, the bioactive agent can be mixed with a gel-like carrier prior to injection into the scaffold.

Following surgical placement, an implant wherein the biocompatible scaffold is devoid of any bioactive agent can be infused with biological agent(s), or an implant wherein the scaffold includes at least one bioactive agent can be augmented with a supplemental quantity of the bioactive agent. One method of incorporating a bioactive agent within a surgically installed implant is by injection using an appropriately gauged syringe.

The amount of the bioactive agent included with a biocompatible scaffold will vary depending on a variety of factors, including the size of the scaffold, the material from which the scaffold is made, the porosity of the scaffold, the identity of the biologically component, and the intended purpose of the tissue repair implant. One skilled in the art can readily determine the appropriate quantity of bioactive agent to include within a biocompatible scaffold for a given application in order to facilitate and/or expedite the healing of tissue. The amount of bioactive agent will, of course, vary depending upon the identity of the bioactive agent and the given application.

The following non-limiting examples are illustrative of the principles and practice of this invention. Numerous additional embodiments within the scope and spirit of the invention will become apparent to those skilled in the art.

Example 1

Cellular migration and new matrix formation of bovine minced meniscal tissue (BMT) into a small intestine submucosa (SIS) tissue scaffold was evaluated and compared. Meniscal tissue was harvested from the white and red-white zone of an adult bovine menisci, and the tissue was minced to form a viable tissue source. A scaffold was prepared from a small intestine submucosa (SIS), and a slit was made in the scaffold to form a pocket. The minced tissue was loaded at 20 mg/cm$^2$ into the SIS scaffold through the slit to form a composite implant. The composite implant was placed in a pocket created in the hemithorax through one skin incision of a mouse. Tacking sutures of 5-0 Ethibond Excel® were used to tack the skin to musculature around each composite implant to prevent subcutaneous migration.

After 4 weeks, the composite implant was prepared for histological evaluation by fixing the implant in 10% buffered formalin, sectioning the implant to form samples, and staining the samples with Hematoxylin/Eosin (H/E). A photomicrograph of the composite implant is shown in FIG. 8B, which can be compared to a photomicrograph of a control sample shown in FIG. 8A. The control was prepared using the same aforementioned procedure, however minced tissue was not loaded into the scaffold.

Figure 8A:
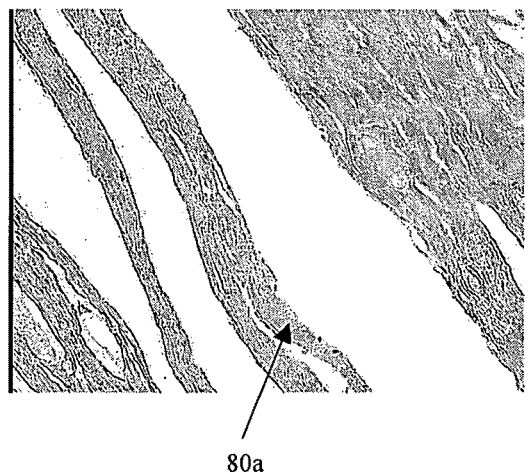
FIG. 8A is a photomicrograph of a small intestine submucosa (SIS) composite implant serving as a control.
Figure 8B:
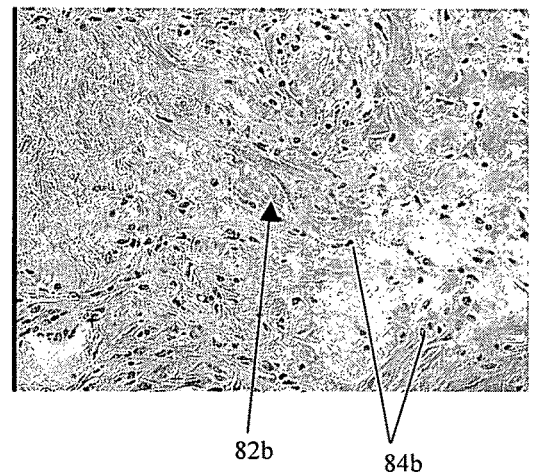
FIG. 8B is a photomicrograph of an SIS composite implant having a pocket containing a viable tissue formed from bovine minced meniscal tissue (BMT), showing native meniscal tissue cells migrating into the implant.

FIG. 8A shows the control tissue scaffold 80a having no native tissue cells. FIG. 8B, on the other hand, shows native meniscal tissue cells 84b that have migrated into the implant and that are present between the minced BMT 82b, and it also shows the minced BMT 82b being remodeled by the native meniscal tissue cells 84b.

Example 2

Cellular migration and new matrix formation of bovine minced meniscal tissue (BMT) into a small intestine submucosa (SIS) tissue scaffold was evaluated and compared. Meniscal tissue was harvested from the white and red-white zone of adult bovine menisci, and the tissue was minced to form a viable tissue source. A scaffold was prepared from a small intestine submucosa (SIS), and a slit was made in the scaffold to form a pocket. The minced tissue was combined with platelet rich plasma (PRP), and the composition was loaded into the SIS scaffold at 20 mg/cm$^2$ through the slit to form a composite implant. The composite implant was placed in a pocket created in the hemithorax through one skin incision of a mouse. Tacking sutures of 5-0 Ethibond Excel® were used to tack the skin to musculature around each composite implant to prevent subcutaneous migration.

Figure 8C:
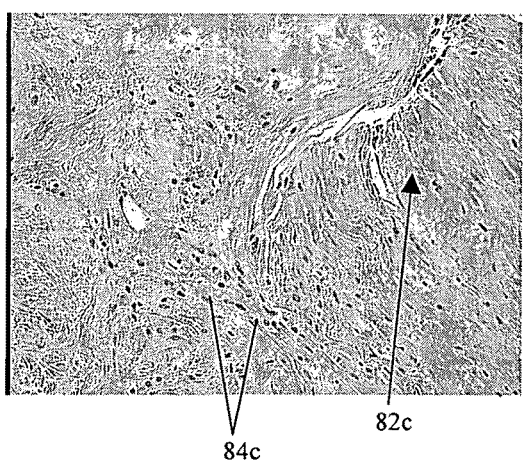
FIG. 8C is a photomicrograph of an SIS composite implant having a pocket containing a viable tissue formed from BMT and platelet rich plasma (PRP), showing improved native tissue cell migration and integration into the implant.

After 4 weeks, the composite implant was prepared for histological evaluation by fixing the implant in 10% buffered formalin, sectioning the implant to form samples, and staining the samples with Hematoxylin/Eosin (H/E). A photomicrograph of the composite implant is shown in FIG. 8C. Reference number 82c shows the minced BMT and PRP being remoded by native meniscal tissue cells 84c that have migrated into the implant.

Example 3

Cellular migration and new matrix formation of bovine minced meniscal tissue (BMT) into a small intestine submucosa (SIS) tissue scaffold was evaluated and compared. Meniscal tissue was harvested from the white and red-white zone of adult bovine menisci, and the tissue was minced. PRP was added to the minced BMT. A viable tissue source was then prepared by combining the BMT and PRP with a bioresorbable polymer scaffold (referred to as "FPV") in a 50:50 ratio. The resorbable scaffold used was a lyophilized foam scaffold (65% polyglycolic acid/35% Polycaprolactone) reinforced with nonwoven fibers (mixture of PDS [Polydioxanone] and Vicryl). A scaffold was prepared from a small intestine submucosa (SIS), and a slit was made in the scaffold to form a pocket. The viable tissue source of FPV, BMT, and PRP was loaded at 20 mg/cm$^2$ into the SIS scaffold through the slit to form a composite implant. The composite implant was placed in a pocket created in the hemithorax through one skin incision of a mouse. Tacking sutures of 5-0 Ethibond Excel® were used to tack the skin to musculature around each composite implant to prevent subcutaneous migration.

Figure 8D:
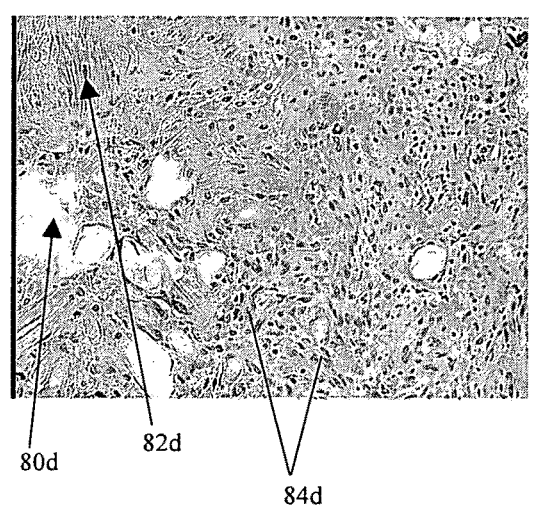
FIG. 8D is a photomicrograph of an SIS composite implant, having a pocket containing a viable tissue source that was prepared by combining the BMT and PRP with a bioresorbable polymer scaffold (referred to as "FPV") in a 50:50 ratio, showing improved native meniscal tissue cell migration and integration into the implant.

After 4 weeks, the composite implant was prepared for histological evaluation by fixing the implant in 10% buffered formalin, sectioning the implant to form samples, and staining the samples with Hematoxylin/Eosin (H/E). A photomicrograph of the composite implant is shown in FIG. 8D, which shows a significant amount of native meniscal tissue cell 84d migration into FPV scaffold 80d and around and between the BMT, and PRP tissue source 82d.

Example 4

Cellular migration and new matrix formation of bovine cartilage tissue (BCT) into a small intestine submucosa (SIS) tissue scaffold was evaluated and compared. Cartilage tissue was harvested from the femoral condyles of adult bovine animals, and the tissue was minced. PRP was added to the minced BCT. A viable tissue source was then prepared by combining the BCT and PRP with a bioresorbable polymer scaffold (referred to as "PV") in a 50:50 ratio. The resorbable scaffold used was a nonwoven scaffold (mixture of PDS[Polydioxanone] and Vicryl). A scaffold was prepared from a small intestine submucosa (SIS), and a slit was made in the scaffold to form a pocket. The viable tissue source of PV, BCT, and PRP was loaded at 20 mg/cm$^2$ into the SIS scaffold through the slit to form a composite implant. The composite implant was placed in a pocket created in the hemithorax through one skin incision of a mouse. Tacking sutures of 5-0 Ethibond Excel® were used to tack the skin to musculature around each composite implant to prevent subcutaneous migration.

Figure 8E:
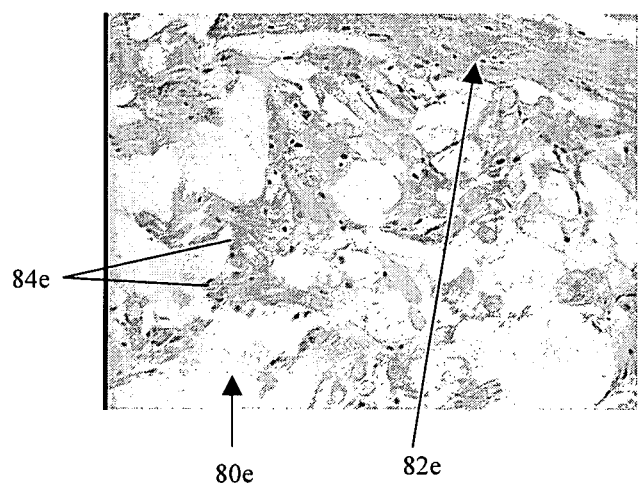
FIG. 8E is a photomicrograph of an SIS composite implant, having a pocket containing a viable tissue source that was prepared by combining the BCT and PRP with a bioresorbable polymer scaffold (referred to as "PV") in a 50:50 ratio, showing improved native tissue cell migration and integration into the implant.

After 4 weeks, the composite implant was prepared for histological evaluation by fixing the implant in 10% buffered formalin, sectioning the implant to form samples, and staining the samples with Hematoxylin/Eosin (H/E). A photomicrograph of the composite implant is shown in FIG. 8E. Some native cartilage tissue cell 84e migration into the tissue scaffold 80e and around and between the viable tissue source 82e is shown.

Example 5

The effect of using a bioactive substance on native meniscal cell migration into a tissue scaffold was evaluated. Menisci were harvested from bovine knees and 4 mm explants were taken from the white and red/white regions. A 2 mm punch biopsy was removed from the center of the explants prior to scaffold insertion. Bioresorbable foam scaffolds (60% Polylactic acid and 40% Polycaprolactone), 2 mm in diameter, were treated either with blood, Platelet Rich Plasma (PRP), or 8 times concentrated PRP, and they were inserted in the center of the explants. The explants with scaffolds were cultured for 2 and 3 weeks under standard cell culture conditions with changes in media occurring every other day. At 2 and 3 weeks, the scaffolds within the explants were removed and cell number was estimated by quantitation of DNA using the CyQuant assay.

Figure 9A:
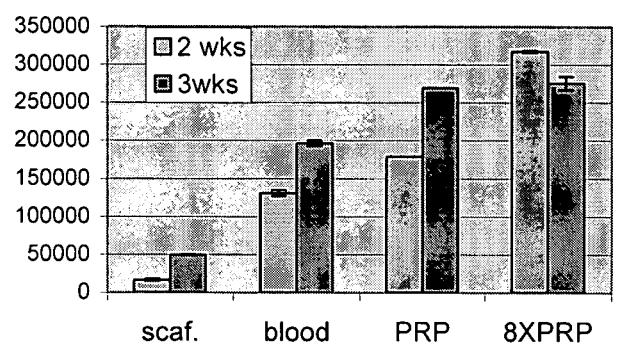
FIG. 9A is a bar chart of viable meniscal tissue cell migration into implants formed from 65% polyglycolic acid/35% polycaprolactone and reinforced with a PDS® mesh, comparing an implant having no bioactive substance to an implant treated with i blood, an implant treated with PRP, and an implant treated with eight times concentrated PRP.

FIG. 9A illustrates the advantages of using a bioactive agent, and in particular it demonstrates that native meniscal cell migration into the scaffold is significantly improved with the use of a bioactive agent, such as a platelet rich plasma (PRP). As shown, the amount of native tissue cells that migrated into the implant after two and three weeks significantly increases in the implants containing PRP as compared to the control and the implant containing blood.

Example 6

The effect of using a bioactive substance on native cell migration into a tissue scaffold was evaluated. Menisci were harvested from bovine knees and 4 mm explants were taken from the white and red/white regions. A 2 mm punch biopsy was removed from the center of the explants prior to scaffold insertion. Bioresorbable foam scaffolds (65% Polyglycolic acid and 35% Polycaprolactone), reinforced with PDS, (Polydioxanone) mesh, 2 mm in diameter, were soaked in 100 µl of CDMP-1 at the concentrations of 10 ng/ml, 100 ng/ml and 300 ng/ml. Scaffolds were lyophilized overnight, such that the growth factor was lyophilized in the scaffold and then inserted in the center of the explants The explants with scaffolds were cultured for 3 weeks under standard cell culture conditions with changes in media occurring every other day. At 2 and 3 weeks, the scaffolds within the explants were removed and cell number estimated by quantitation of DNA using the CyQuant assay.

Figure 9B:
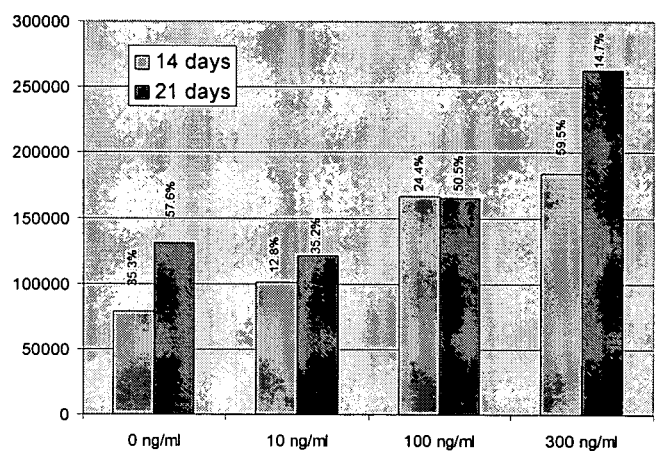
FIG. 9B is a bar chart comparing viable tissue cell migration into implants formed from 65% polyglycolic acid/35% polycaprolactone and reinforced with a PDS® mesh, comparing implants containing viable tissue treated with varying amounts of cartilage-derived morphogenic proteins (CDMP-1)

FIG. 9B demonstrates the amount of native meniscal tissue cells that migrate into an implant formed from 65% polyglycolic acid/35% polycaprolactone reinforced with a PDS® mesh after 14 days and after 21 days. As shown, the implant containing no CDMP-1 and the implant containing only 10 ng/ml of CDMP-1 did not receive as much native tissue cells after 14 and 21 days as the implants containing 100 ng/ml of CDMP-1 and 300 ng/ml of CDMP-1, which showed a significant improvement in native meniscal tissue cell migration.

Example 7

The effect of using a bioactive substance on native cell migration into a tissue scaffold was evaluated. Menisci were harvested from bovine knees and 4 mm explants were taken from the white and red/white regions. A 2 mm punch biopsy was removed from the center of the explants prior to scaffold insertion. Bioresorbable foam scaffolds (65% Polyglycolic acid and 35% Polycaprolactone), reinforced with PDS, (Polydioxanone) mesh, 2 mm in diameter, were soaked in 100 µl of CDMP-1 at the concentrations of 150 ng/ml. Scaffolds were lyophilized overnight, such that the growth factor was lyophilized in the scaffold and then inserted in the center of the explants The explants with scaffolds were cultured for 3 weeks under standard cell culture conditions with changes in media occurring every other day. At 3 weeks, the explants were removed and processed histology for staining with Hematoxylin/Eosin (H/E).

Figure 10A:
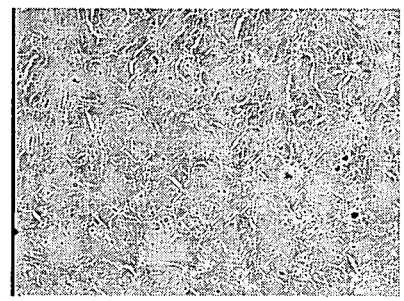
FIG. 10A is a photomicrograph of an implant formed from minced meniscal tissue serving as a control.
Figure 10B:
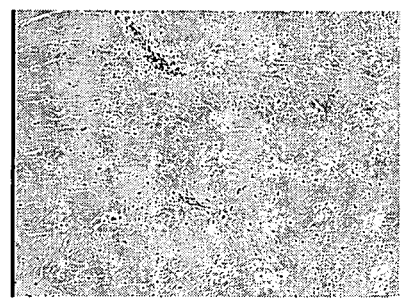
FIG. 10B is a photomicrograph of an implant formed from minced meniscal tissue loaded with CDMP-1, showing native tissue cell migration into the implant.

FIGS. 10A and 10B show a photomicrograph of the explants. FIG. 10A is a photomicrograph of the first explant which was untreated, serving as the control, and FIG. 10B is a photomicrograph of the meniscal explant with CDMP-1. As shown, the explant in FIG. 10B contains a significant amount of native tissue cell as compared to the implant in FIG. 10A.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A composite implant for repairing a tissue defect in a patient, comprising:
    a wedge-shaped porous tissue scaffold formed from a bioresorbable, synthetic polymeric material and including at least one pocket containing finely minced fragments of viable meniscal tissue that are not suspended in a carrier, wherein:
    the tissue scaffold has a first side wall, a second side wall opposed to the first side wall, a top wall, a bottom wall opposed to the top wall, and an end wall that connects the top wall, the bottom wall, the first side wall, and the second side wall;
    the top and bottom walls are joined directly together at an end of the tissue scaffold that is opposite to the end wall;
    the pocket has an opening formed in the end wall; and
    the pocket is closed along the first and second side walls, the top wall, and the bottom wall; and
    the viable meniscal tissue comprises naturally occurring cells and their extracellular matrix, and the naturally occurring cells and their extracellular matrix being native to the viable meniscal tissue.

2. The composite implant of claim 1, further comprising at least one bioactive substance applied to the viable meniscal tissue and effective to stimulate cell growth.

3. The composite implant of claim 2, wherein the bioactive substance is selected from the group consisting of a blood clots, platelet rich plasma, cartilage-derived morphogenic proteins, recombinant human growth factors, and combinations thereof.

4. The composite implant of claim 1, wherein the pocket comprises a hollow interior formed in the tissue scaffold.

5. The composite implant of claim 1, wherein the pocket comprises at least one lumen extending into the tissue scaffold.

6. The composite implant of claim 1, wherein cells from the viable meniscal tissue in the pocket of the scaffold populate at least a portion of the scaffold.

7. The composite implant of claim 1, wherein at least a portion of the scaffold is capable of being populated with cells from the native tissue following implantation.

8. The composite implant of claim 1, wherein the opening is centrally located in the end wall.

9. A composite implant for repairing a tissue defect in a patient, comprising:
    a wedge-shaped porous tissue scaffold having only one pocket formed therein; and
    finely minced fragments of viable cartilage tissue disposed within the one pocket in the scaffold without a carrier, the viable cartilage tissue comprising naturally occurring cells and their extracellular matrix, and the naturally occurring cells and their extracellular matrix being native to the viable cartilage tissue.

10. The composite implant of claim 9, further comprising at least one bioactive substance applied to the viable cartilage tissue and effective to stimulate cell growth.

11. The composite implant of claim 10, wherein the bioactive substance is selected from the group consisting of a blood clots, platelet rich plasma, cartilage-derived morphogenic proteins, recombinant human growth factors, and combinations thereof.

12. The composite implant of claim 9, wherein the tissue scaffold includes top and bottom portions that are at least partially mated to one another.

13. The composite implant of claim 9, wherein the pocket comprises a hollow interior formed in the tissue scaffold.

14. The composite implant of claim 9, wherein the pocket is one lumen extending into the tissue scaffold.

15. The composite implant of claim 9, wherein the tissue fragment has a thickness in the range from about 200 µm to about 3 mm.

16. The composite implant of claim 9, wherein the tissue fragment has a particle size in the range from about 0.5 mm³ to about 3 mm³.

17. The composite implant of claim 9, wherein cells from the viable cartilage tissue in the pocket of the scaffold populate at least a portion of the scaffold.

18. The composite implant of claim 9, wherein at least a portion of the scaffold is capable of being populated with cells from the native tissue following implantation.

19. The composite implant of claim 9, wherein the wedge shape of the tissue scaffold tapers down from a front end thereof to a back end thereof, and the one pocket has an opening formed in the front end of the tissue scaffold.

20. The composite implant of claim 19, wherein a first surface extends from the front end of the tissue scaffold to the back end of the tissue scaffold; and
    a second surface that is opposed to the first surface extends from the front end of the tissue scaffold to the back end of the tissue scaffold and is joined directly to the first surface at the back end of the tissue scaffold.

21. A method for repairing defective tissue, comprising:
    obtaining a viable cartilage tissue comprising naturally occurring cells and their extracellular matrix;
    mincing the viable cartilage tissue, with its native naturally occurring cells and extracellular matrix, to form finely minced tissue particles and, without further processing of the finely minced tissue particles, loading the finely minced tissue particles into at least one pocket of a tissue scaffold, wherein:
    the tissue scaffold is formed from a bioresorbable, synthetic polymeric material having the at least one pocket formed therein and adapted to contain a viable cartilage tissue,
    the tissue scaffold has a first side wall, a second side wall opposed to the first side wall, a top wall, a bottom wall opposed to the top wall, and an end wall that connects the top wall, the bottom wall, the first side wall, and the second side wall, the top and bottom walls are joined directly together at an end of the tissue scaffold that is opposite to the end wall, the at least one pocket includes an opening formed in one of the top wall, the bottom wall, and the end wall, and the at least one pocket being closed along a remainder of the first and second side walls, the top and bottom walls, and the end wall; and implanting the tissue scaffold with the finely minced tissue particles disposed therein at a defect site in a patient's body such that native tissue surrounding the tissue scaffold abuts the end wall so as to abut the opening formed in the end wall and thereby maintaining the finely minced tissue particles in the at least one pocket.

22. The method of claim 21, further comprising the step of applying at least one bioactive substance to the finely minced tissue particles to stimulate cell growth.

23. The method of claim 22, wherein the bioactive substance is selected from the group consisting of a blot clots, platelet rich plasma, cartilage-derived morphogenic proteins, recombinant human growth factors, and combinations thereof.

24. The method of claim 21, wherein the tissue scaffold is substantially wedge-shaped and the pocket comprises a hollow interior formed in the tissue scaffold.

25. The method of claim 21, wherein the tissue scaffold is substantially wedge-shaped, and the pocket comprises at least one lumen extending into the tissue scaffold.

26. The method of claim 21, wherein the tissue scaffold includes at least one surface feature formed thereof to promote blood vessel formation.

27. The method of claim 26, wherein the at least one surface feature comprises a plurality of channels formed on an outer surface of the tissue scaffold.

28. The method of claim 21, wherein cells from the viable cartilage tissue in the pocket of the scaffold populate at least a portion of the scaffold.

29. The method of claim 21, wherein at least a portion of the scaffold is populated with cells from the native tissue following implantation.

* * * * *